(12) United States Patent
Taft et al.

(10) Patent No.: US 7,005,110 B2
(45) Date of Patent: Feb. 28, 2006

(54) METHOD AND APPARATUS FOR PREPARING TISSUE SAMPLES FOR SECTIONING

(75) Inventors: Scott Taft, Oro Valley, AZ (US); Kurt Reinhardt, Tucson, AZ (US); Miroslav Holubec, Tucson, AZ (US); David Bryant, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 350 days.

(21) Appl. No.: 10/029,658

(22) Filed: Dec. 20, 2001

(65) Prior Publication Data

US 2003/0119200 A1    Jun. 26, 2003

(51) Int. Cl.
*A61B 10/00* (2006.01)

(52) U.S. Cl. .............. 422/102; 422/68.1; 422/104; 436/174; 436/807; 435/40.5; 435/40.52; 600/562; 600/564; 606/167; 206/557; 206/562; 206/563; 206/564; 206/524.1

(58) Field of Classification Search ............ 436/174, 436/807; 435/40.5, 40.52; 600/562, 564; 606/167; 206/557, 562, 563, 564, 524.1; 422/68.1, 102, 104

See application file for complete search history.

(56) References Cited

U.S. PATENT DOCUMENTS

| 3,411,185 A | 11/1968 | Pickett et al. |
| 3,674,396 A * | 7/1972 | McCormick ............... 425/117 |
| 3,982,862 A | 9/1976 | Pickett et al. |
| 4,557,903 A | 12/1985 | McCormick |
| 4,801,553 A | 1/1989 | Owen et al. |
| 5,080,869 A | 1/1992 | McCormick |

(Continued)

FOREIGN PATENT DOCUMENTS

| EP | 0 142 575 | 5/1985 |
| GB | 1582988 | * 9/1976 |

OTHER PUBLICATIONS

"Tissue Embedding Unit", Alabama Research and Development Product Catalogue, Jan. 2001, www.alspi.com/embed.htm.

"HistoGel Specimen Processing Gel" Brochure, Richard-Allan Scientific, Publication date Nov. 1999.

(Continued)

*Primary Examiner*—Monique T. Cole
(74) *Attorney, Agent, or Firm*—Hayes Soloway P.C.

(57) ABSTRACT

The present invention provides a more efficient and faster way to prepare tissue samples for sectioning. More particularly, in accordance with the present invention, a tissue sample is embedded in a porous embedding media in a desired orientation, processed, and sectioned all while being held in the porous embedding media. The post-tissue processing step of manual embedding in paraffin is eliminated from the process.

51 Claims, 6 Drawing Sheets

U.S. PATENT DOCUMENTS

| | | | | |
|---|---|---|---|---|
| 5,269,671 A | * | 12/1993 | McCormick | 425/117 |
| 5,312,758 A | * | 5/1994 | Ahlqvist | 436/63 |
| 5,424,040 A | * | 6/1995 | Bjornsson | 422/101 |
| 5,427,742 A | * | 6/1995 | Holland | 422/102 |
| 5,432,056 A | | 7/1995 | Hartman et al. | |
| 5,560,956 A | | 10/1996 | Schmehl | |
| 5,665,398 A | | 9/1997 | McCormick | |
| 5,821,115 A | * | 10/1998 | Graupner | 435/283.1 |
| 5,843,700 A | | 12/1998 | Kerrod et al. | |
| 5,928,934 A | | 7/1999 | McCormick | |
| 6,017,476 A | | 1/2000 | Renshaw | |
| 6,372,512 B1 | * | 4/2002 | Kerschmann | 436/174 |
| 6,395,234 B1 | * | 5/2002 | Hunnell et al. | 422/101 |
| 6,815,199 B1 | | 11/2004 | Kubota | 435/307.1 |

OTHER PUBLICATIONS

Histologic Technical Bulletin for Histotechnology, Sakura, vol. XXXI, No. 2, Dec. 1999.

* cited by examiner

US 7,005,110 B2

METHOD AND APPARATUS FOR PREPARING TISSUE SAMPLES FOR SECTIONING

FIELD OF THE INVENTION

The present invention relates to preparation of tissue samples for histological examination. The invention has particular utility in preparing tissue samples for microtome sectioning prior to microscopic examination, and will be described in connection with such utility, although other utilities are contemplated.

BACKGROUND OF THE INVENTION

Conventionally, tissue specimens are prepared for microtome sectioning in two sequential stages. In the first stage the tissue specimen is preserved by chemical fixation and the impregnation of paraffin. The specimen is typically held in a cassette to maintain control and segregate it from other samples. The specimen is placed in a fixation solution, typically neutral buffered formalin, to preserve the chemical structure of the tissue. The specimen is then subjected to a series of solvents, typically alcohols and xylene followed by molten paraffin. The solvents remove the water content of the tissue, and provide a bridge to allow the molten paraffin to penetrate the sample and structurally support it. At the end of the first stage the tissue specimen is loose in the cassette, chemically fixed and impregnated with paraffin. In the second stage the tissue specimen is oriented and embedded in a paraffin block in preparation for sectioning. The specimen is placed and oriented in the bottom of a mold and molten paraffin is poured over the specimen. A jig or fixture for attachment to the microtome is placed in the top of the mold and additional molten paraffin is poured to embed this fixture to the paraffin block. The paraffin block is allowed to cool and solidify. The paraffin block is then removed from the mold, exposing the tissue specimen, and then mounted in the clamp of a microtome for sectioning of the specimen.

It is important that the specimen is accurately positioned in the embedding mold prior to the paraffin embedding step, so that sectioning of the specimen occurs along appropriate planes to reveal the desired cell structure. Presently, accurate positioning of the specimen is achieved by setting the specimen in a desired position in the embedding mold, and allowing a few drops of molten paraffin wax to fall on the specimen to set the specimen in the desired position. Alternatively, a few drops of molten paraffin wax are placed in the bottom of the embedding mold, and the specimen is set in desired position in the still molten paraffin wax. The molten paraffin wax is allowed to cool and solidify. The solidified paraffin wax holds the specimen in the required position through the second stage, after which more molten paraffin wax is added to the cassette or mold to fully embed the specimen. In place of paraffin wax, molten nitrocellulose, gelatin, and various resins have been used to embed the specimen in a desired orientation through the first stage.

Various attempts to improve the preparation of tissue samples for sectioning primarily have involved modifications to the molds or cassettes. See, for example, U.S. Pat. Nos. 3,982,862; 4,557,903; 4,801,553; 5,080,869; and 6,017,476, which are exemplary.

SUMMARY OF THE INVENTION

The present invention provides a more efficient and faster way to prepare tissue samples for sectioning. More particularly, in accordance with the present invention, a tissue sample is embedded in a porous embedding media in a desired orientation, processed, and sectioned all while being held in the porous embedding media. The post-tissue processing step of manual embedding in paraffin is eliminated from the process.

BRIEF DESCRIPTION OF THE DRAWINGS

Various features and advantages of the present invention will be seen from the following detailed description, taken in conjunction with the following drawings, wherein like numerals depict like parts, and wherein.

DETAILED DESCRIPTION OF THE PREFERRED EMBODIMENTS

Figure 1:
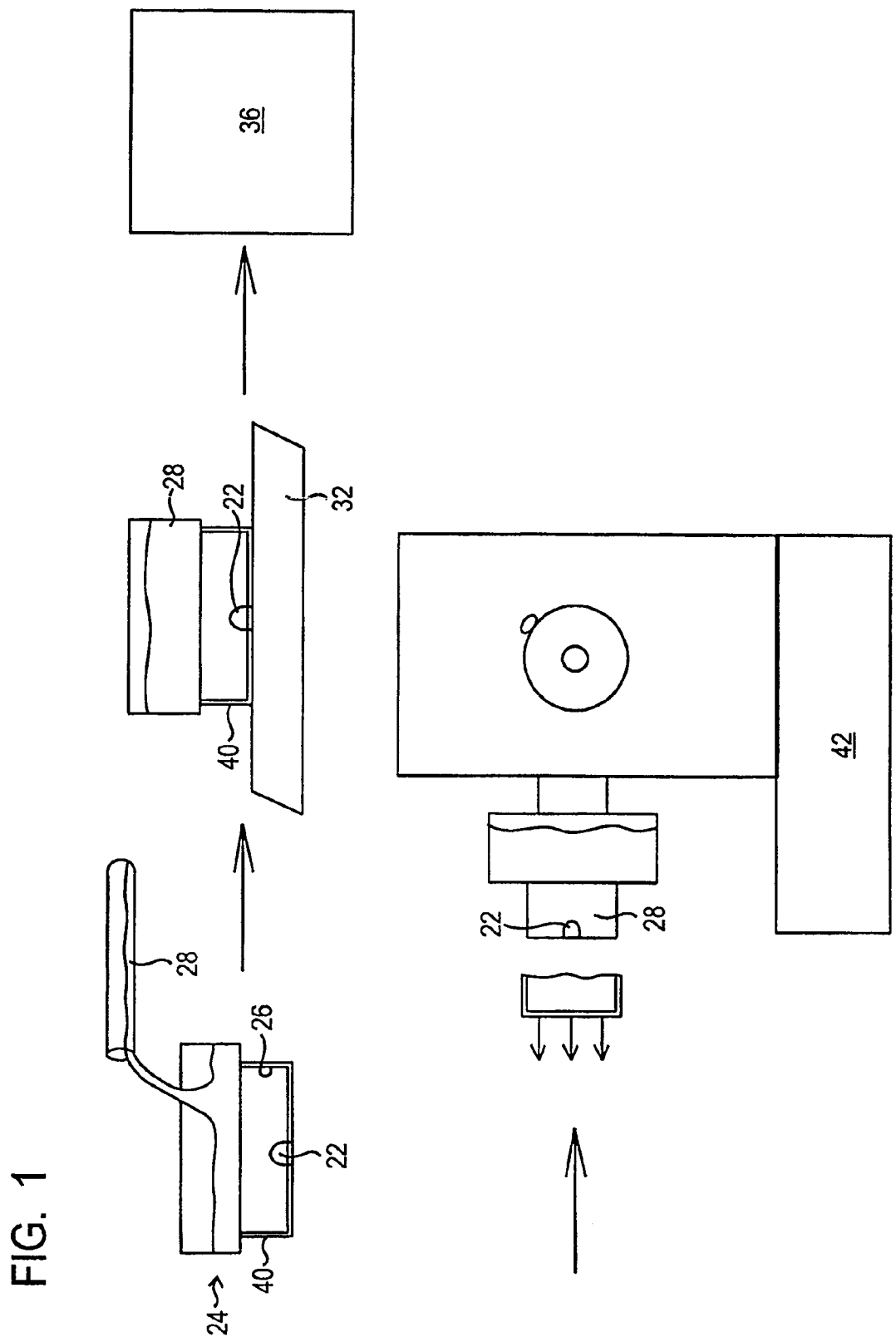
FIG. 1 is a diagrammatic flow chart showing a first method for orienting and processing a tissue sample in accordance with the present invention.

FIG. 1 is a diagrammatic flow chart showing a first method for orienting and processing a tissue sample for sectioning in accordance with the present invention. The technician obtains a tissue sample 22 from the examining doctor, nurse, or specialist. The technician typically will be given instructions as to how the tissue sample should be oriented for sectioning on a microtome or other cutting device. The technician orients the tissue sample 22 in a modified cassette-mold combination 24, which is lined with a filter paper 26, or the like. The technician then embeds the tissue sample 22 in the cassette 24 by filling the cassette with molten porous embedding media 28. The porous embedding media should be a material which is normally solid at room temperature and at tissue processing temperatures, and should have a melting point or liquidus point which is below the temperature at which the tissue sample would become denatured or otherwise changed by heat. The porous embedding media also is a material that is porous to treating solutions commonly used in processing and fixing tissues, e.g. acetic acid, acetone, chromic or picric acid, alcohols, aldehydes, mercuric chloride, osmium tetroxide, potassium dichloride, xylene, etc. Applicant has found that low melting point agarose, i.e. agarose having a melting point in the range of about 55 to 65° C., works particularly well as a porous embedding media. Currently preferred is Histogel™ brand of hydroxyethyl agarose available from Wayne Holland.

The technician fills the cassette/mold combination 24 with molten porous embedding media 28 until the specimen is completely covered. Generally, but not necessarily, the porous embedding media is added to fill the cassette/mold combination to the top. The cassette/mold combination containing the tissue sample and the liquid embedding media may be cooled on a cold plate 32 to solidify the porous embedding media, or simply left to cool to room temperature.

The cassette/mold combination containing the embedded tissue sample is then placed in a tissue processor 36 for conventional fixing and processing. The cassette/mold combination must be oriented in the tissue processor as shown in FIG. 1, with the tissue sample and filter paper on the bottom.

During conventional automated processing the tissue sample as well as the porous embedding media are infiltrated with paraffin then allowed to cool to room temperature. This forms the paraffin block that contains the tissue oriented in the position the technician originally positioned it in After the tissue sample is processed, the bottom of the cassette 40 is removed, and the filter paper stripped from the paraffin block, exposing the embedded tissue. The cassette/mold combination then is coupled to a microtome 42 for tissue sectioning.

A feature and advantage of the present invention that results from using a porous embedding media during fixing and pre-processing, is that the post-processing paraffin wax embedding step is eliminated. In other words, one step in the process is eliminated, along with the technician time, equipment, material, energy and environmental costs associated with the paraffin wax embedding step. Moreover, tissue orientation is assured through the entire process, which is extremely critical for small biopsy examination.

Figure 2:
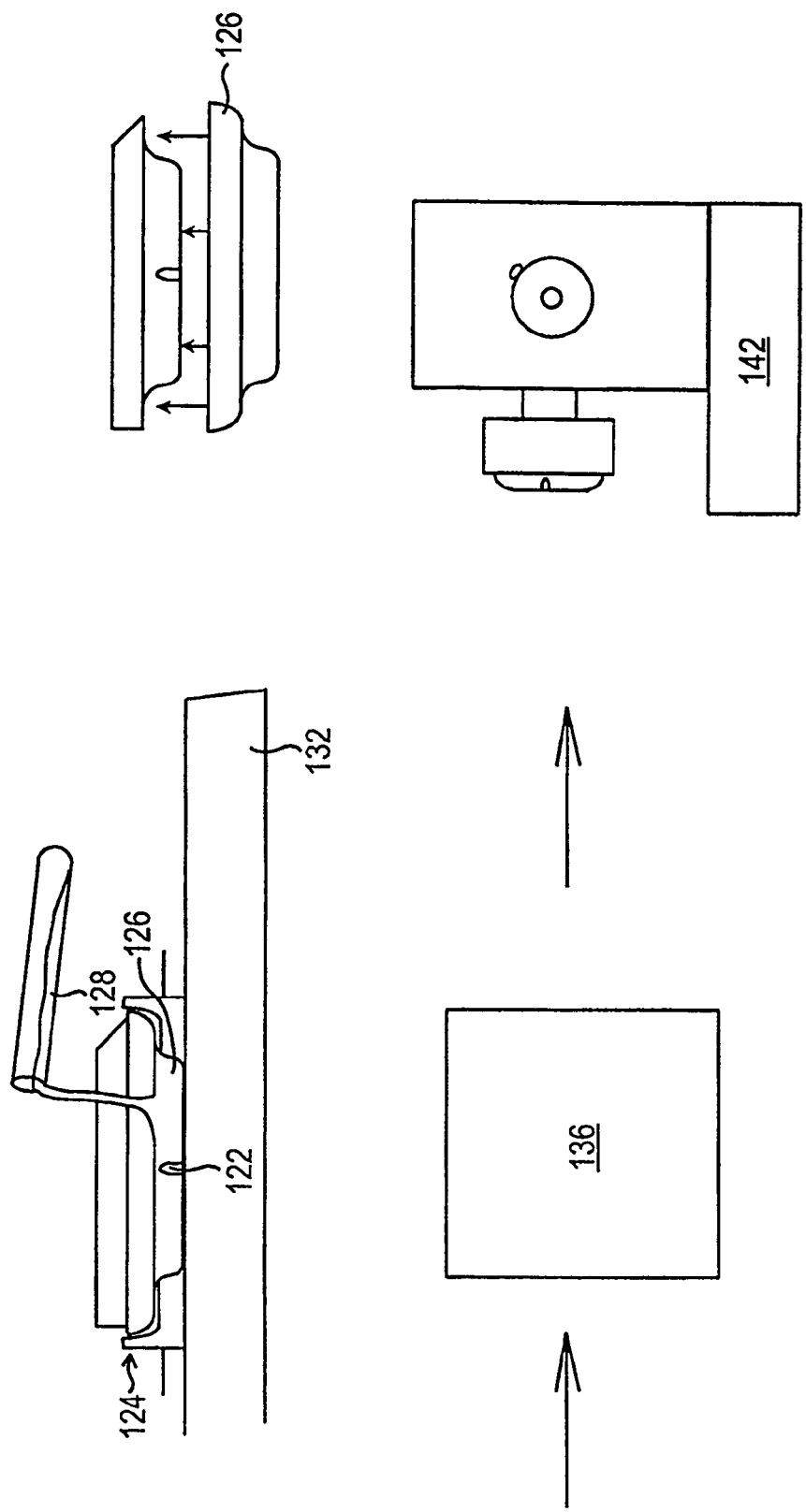
FIGS. 2–4 are views similar to FIG. 1, showing second and third method for orienting and processing a tissue sample in accordance with the present invention.

Referring to FIG. 2, there is illustrated a second method of orienting and processing a tissue sample for sectioning in accordance with the present invention. The technician obtains a tissue sample 122 from the examining doctor, nurse or specialist. The technician typically will be given instructions as to how the tissue sample should be oriented for sectioning on a microtome or other cutting device. The technician orients the tissue sample 122 on the bottom of a two-piece processing cassette 124 which includes a removable plastic or metal bottom dish 126. The technician then embeds the tissue sample 122 in the cassette 124 by filling the cassette with molten porous embedding media 128. As before, the porous embedding media should be a material which is normally solid at room temperature and at tissue processing temperatures, and should have a melting point or liquidus point below the temperature at which the tissue sample would become denatured or otherwise changed by heat. The porous embedding media also should be a material that is porous to treating solutions commonly used in fixing and dehydrating tissues. As before, agarose has been found to be a particularly preferred porous embedding media.

The technician fills the cassette/mold combination 124 with molten porous embedding media 128 until the specimen is completely covered. The cassette containing the tissue sample and liquid porous embedding media may be cooled on a cold plate 132 to solidify the porous embedding media. Thereafter, the plastic or metal bottom dish 126 is separated from the remainder of the cassette to expose the embedded tissue sample, which is then passed to a tissue processor 136 for conventional fixing and processing. After the tissue sample is processed, the cassette then is coupled to a microtome 142 for tissue sectioning.

As before, by using a porous embedding media pre-processing and fixing, the post-processing paraffin wax embedding step is eliminated.

Figure 3:
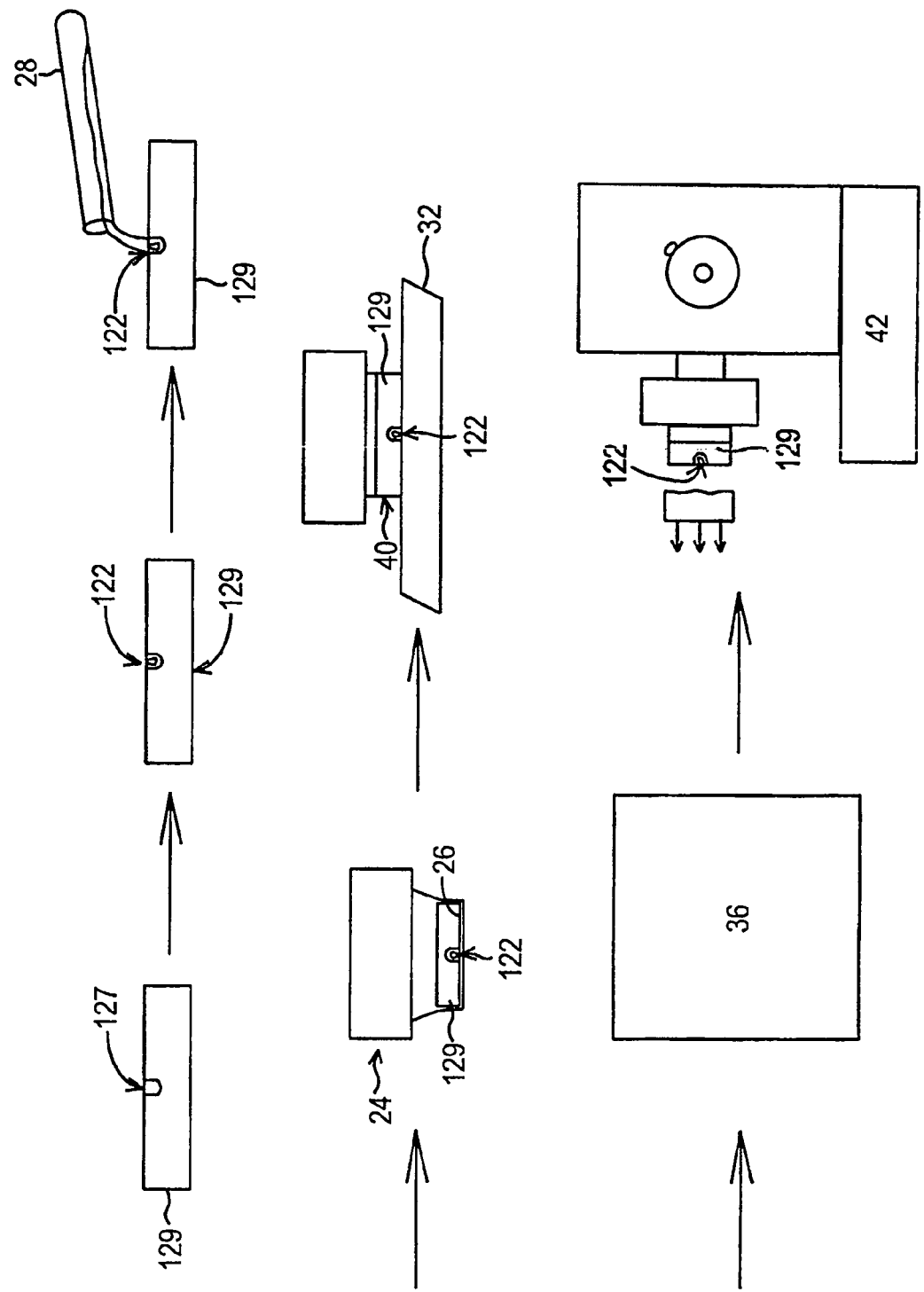

FIG. 3 shows yet another method of orienting and processing a tissue sample for sectioning in accordance with the present invention. FIG. 3 is similar to FIG. 1, in which, however, in place of porous embedding media 28, a pre-formed porous embedding block 129 is employed. The embedding block 129 preferably comprises a phenolic foam which is commercially available as a floral mounting block. A phenolic foam is preferred since it is inert and resistant to the liquids typically employed in tissue fixing and processing, yet is porous to the liquids, widely available, low cost, and easy to cut and shape. The pre-formed embedding block 129 is cut or shaped to fit into the bottom of the cassette/mold combination 24 which is lined with filter paper 26 or the like. However, prior to placing the pre-formed embedding block 129 into the cassette/mold combination, the technician forms a hole or depression 127 in the block 129, e.g. by cutting, drilling or punching a blind hole or slot, for accommodating the tissue sample in the desired orientation. The tissue sample 122 is placed in the hole 127. Porous embedding media 28 may be placed in the hole 127 and allowed to solidify to maintain the orientation of the tissue sample 122. The pre-formed embedding block 129 carrying the tissue sample 122 in desired orientation is then placed in the cassette. The cassette containing the embedded tissue sample is then passed to a tissue processor 36 for conventional fixing and processing, as before, prior to sectioning.

Figure 4:
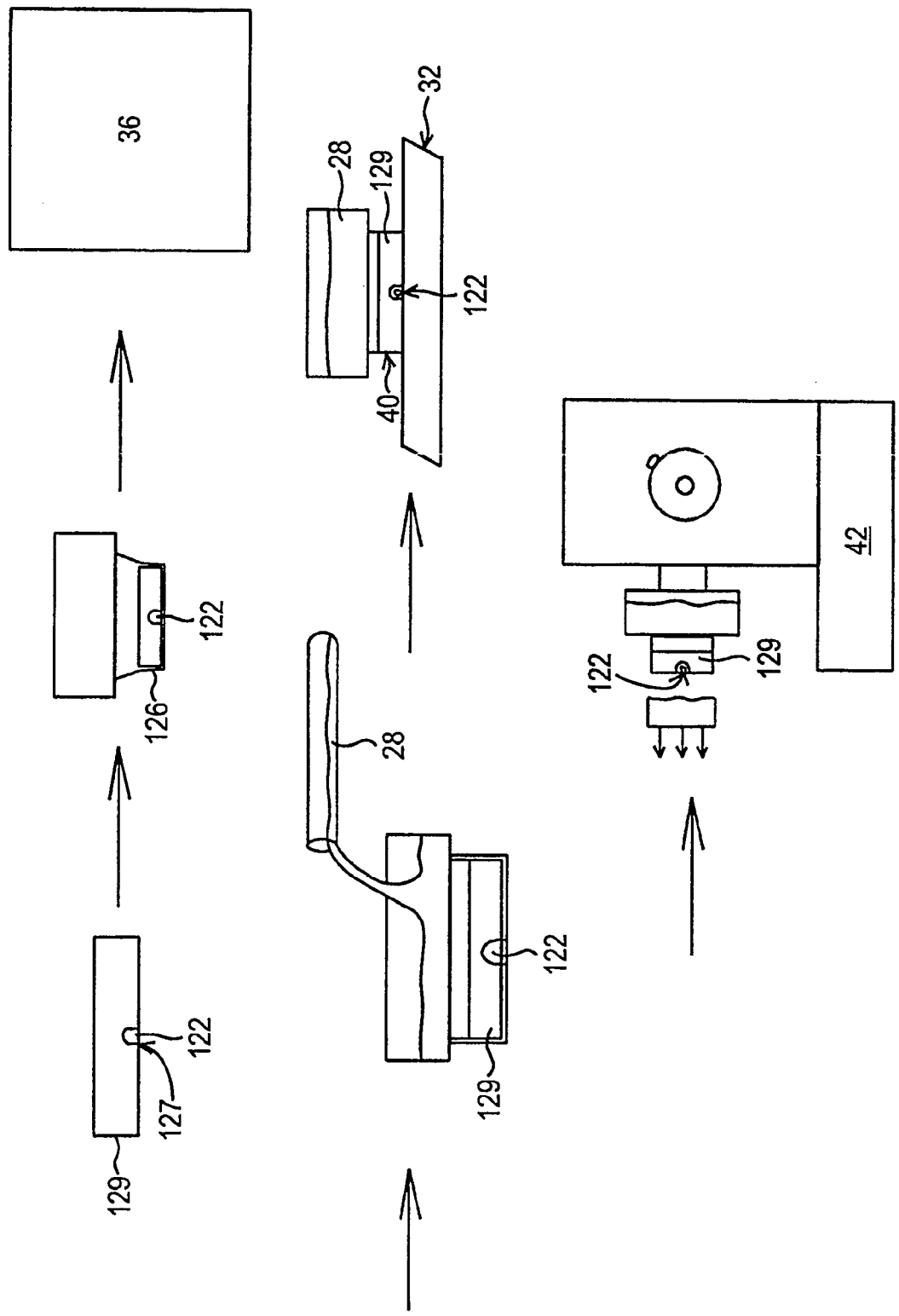

Alternatively, as shown in FIG. 4, the embedding block carrying the tissue sample may be placed in a cassette and passed directly to a tissue processor for conventional fixing and processing. After the tissue sample is processed, the sample and pre-formed embedding block may then be infiltrated and embedded in molten embedding media which may be a conventional paraffin wax, agarose, nitrocellulose, gelatin, or a resin, and the molten embedding media solidified by cooling, and the embedded sample then sectioned, as before.

While the embodiment of FIG. 4 doesn't have the advantages of the FIGS. 1–3 embodiments of eliminating the post-processing embedding step, the use of a pre-formed porous foam embedding media has advantages in that less paraffin wax or other embedding media is used. Also, the pre-formed foam embedding media may be supplied at the tissue grossing lab so that the Pathologist or assistant could precisely position the tissue sample in a desired orientation, thus eliminating possible miscommunication with the technician.

Referring to FIGS. 5–8, there is shown an improved cassette 48 for use in accordance with the present invention. It would be appreciated, however, that the cassette as described below, advantageously may be employed in connection with a conventional paraffin wax impregnation process.

Figure 6:
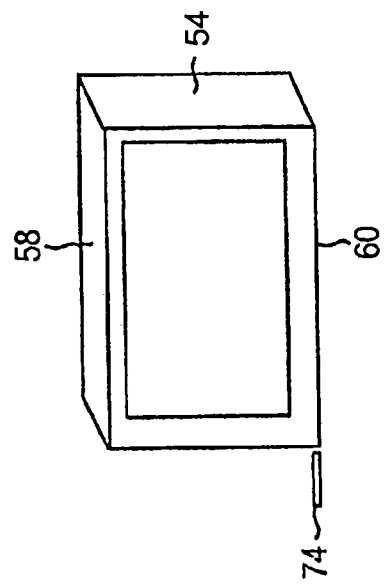
FIG. 6 is a top plan view of the embedding cassette of FIG. 5.
Figure 5:
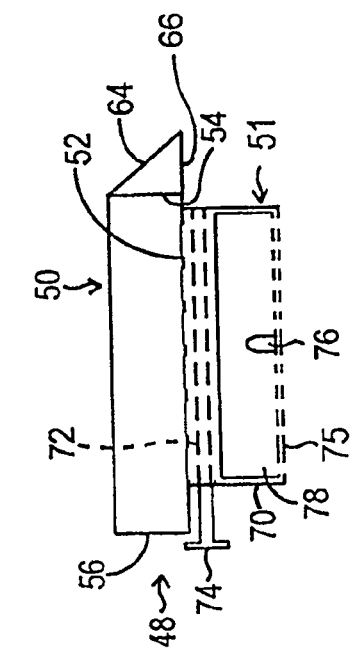
FIG. 5 is a side elevational view, in section, of an embedding cassette in accordance with another preferred embodiment of the present invention.
Figure 7:
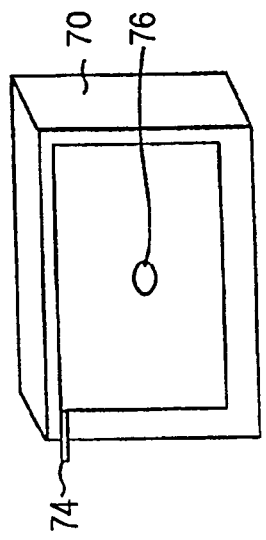
FIG. 7 is a bottom view of the embedding cassette of FIG. 5.
Figure 5A:
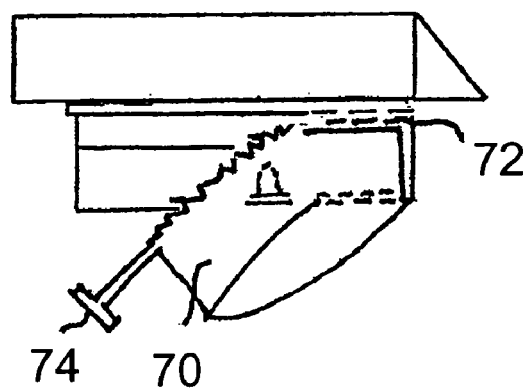
FIG. 5a is a view similar to FIG. 5 showing the cassette side and bottom wall elements partially removed along frangible tear lines using a pull tab.

Referring specifically to FIGS. 5, 5a and 6, the cassette 48 comprises a two-piece body including a top portion 50 and a bottom portion 51. Top portion 50 has a perforated bottom wall 52, a front wall 54, a back wall 56, and two side walls 58, 60. Preferably, the front wall 54 includes an angled extension wall 64, which provides a writing surface on which a sample identification label may be affixed. If desired, barcode indicia may be affixed to the underside surface 66 of extension wall 64. Bottom portion 51 is snap or friction mounted to top portion 50, and comprises a perforated bottom wall 75 and a bridging side wall 70 which spaces the bottom wall 75 from the top portion 50, and serves to contain molten porous embedding media. Bridging side wall 70 includes a pair of tear lines or lines of weakness 72 and a pull tab 74. The cassette including the top and bottom portions 50, 51 are made of a suitable plastic material compatible with the intended processing and fixing.

Use of the cassette 48 above described will now be discussed. Again referring to FIG. 5, the technician obtains a tissue sample 76 from the examining doctor, nurse, or specialist. The technician will typically be given instructions as to how the tissue sample should be oriented for sectioning on a microtome or other cutting device. The technician obtains a pre-formed embedding block 78, and forms an opening in the block 78 for the tissue sample, e.g. by cutting, drilling or punching a blind hole or slot. As before, the embedding block 78 preferably comprises a phenolic foam such as a floral mounting block. As mentioned supra, a phenolic foam mounting block is preferred since it is inert and resistant to the liquids typically employed in tissue processing and fixing, porous, widely available, low cost and easy to cut and shape. The embedding block 78 is cut or shaped to fill, at least in part, the bottom portion 51 of cassette 48. The embedding block with the tissue sample mounted therein is placed into the bottom portion 51 of cassette 48 with the tissue facing the outside of the cassette. The top portion 50 is then snapped or fitted to the bottom portion 51.

Figure 8:
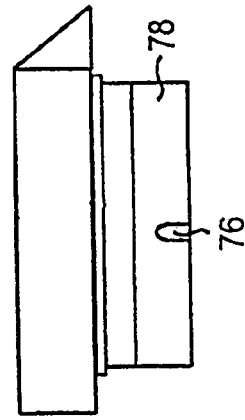
FIG. 8 is a view, similar to FIG. 5, of the embedding cassette of FIG. 5 after embedding and processing, with the bottom portion of the cassette removed, and ready for sectioning.

The tissue sample may be automatically processed to remove water and fix the tissue sample, etc. using known processing techniques, the last step being the paraffin infiltration step where the tissue sample and porous embedding media are infiltrated with paraffin and allowed to solidify. Bridging side wall 70 and bottom wall 75 are then peeled off the cassette along the line of weakness 72 (see FIG. 5*a*), to expose the embedded tissue sample in the foam block (FIG. 8). The sample may then be sectioned on a microtome.

Various changes may be made in the invention. For example, a tissue sample may be oriented in a pre-formed embedding block and then processed in a conventional cassette. Also, the two-part cassette with a removable bridging side wall of FIGS. 5–8 may be employed in a conventional two-stage fixing and embedding process.

It should be understood that, while the present invention has been described in detail herein, the invention can be embodied otherwise without departing from the principles thereof, and such other embodiments are meant to come within the scope of the present invention as defined in the following claim(s):

We claim:

1. A cassette having a hollow for receiving and retaining a tissue specimen for fluid treatment preparatory to histological examination, comprising a top portion having a perforated bottom wall and a bottom portion snap or friction mounted to the top portion, the bottom portion having side and bottom walls removable along a frangible tear line in said side walls.

2. The cassette of claim 1, wherein said removable side wall bridges said top and bottom portions.

3. The cassette of claim 1, wherein said removable side wall includes a pair of frangible tear lines.

4. The cassette of claim 1, wherein said removable side wall includes a projecting tab to facilitate removal of said side wall.

5. The cassette of claim 1, wherein said top and bottom portions are molded of a synthetic plastic material.

6. The cassette of claim 1, further comprising a pre-formed foam block in said hollow.

7. The cassette of claim 1, further comprising agarose in said hollow.

8. The cassette of claim 1, further comprising both agarose and a pre-formed foam block in said hollow.

9. The cassette of claim 6, further comprising filter paper positioned in said hollow to retard egress of molten paraffin.

10. A method for preparing a tissue sample for analysis, comprising the steps of:
    (a) orienting the tissue sample in the cassette of claim 1;
    (b) embedding an oriented tissue sample in a porous embedding media; and
    (c) directly processing the embedded tissue sample with tissue processing reagents while maintaining the original orientation of the sample without a post-processing paraffin-embedding step.

11. The method of claim 10, wherein the porous embedding media comprises agarose.

12. The method of claim 10, wherein the porous embedding media comprises a pre-formed foam.

13. The method of claim 12, wherein the tissue sample is oriented in an opening or depression formed in said pre-formed foam.

14. The method of claim 13, including the step of forming said opening or depression by cutting, drilling, punching or molding.

15. The method of claim 13, wherein the tissue sample is embedded flush with or below an outer surface of the pre-formed foam.

16. The method of claim 13, wherein the pre-formed foam comprises a preformed block of phenolic foam.

17. The method of claim 11, wherein said agarose has a melting point in the range of about 55 to 65° C.

18. The method of claim 10, further including the step of sectioning the embedded tissue sample following processing.

19. The method of claim 10, wherein said tissue processing reagents are selected from the group consisting essentially of aqueous formalin, water, xylene, alcohol and paraffin.

20. A hollow cassette for receiving and retaining a tissue specimen for fluid treatment preparatory to histological examination, comprising a top portion having a perforated bottom wall and a bottom portion snap or friction mounted to the top portion, the bottom portion having side and bottom walls removable along a frangible tear line in said side walls, the hollow being filled, at least in part, by a porous embedding medium.

21. The cassette of claim 20, wherein said porous embedding medium comprises agarose and/or a pre-formed foam.

22. The cassette of claim 20, wherein said removable side wall bridges said top and bottom portions.

23. The cassette of claim 20, wherein said removable side wall includes a pair of frangible tear lines.

24. The cassette of claim 20, wherein said removable side wall includes a projecting tab to facilitate removal of said side wall.

25. The cassette of claim 20, wherein said top and bottom portions are molded of a synthetic plastic material.

26. The cassette of claim 21, and further comprising filter paper positioned within the cassette to retard egress of molten paraffin.

27. The cassette of claim 21, wherein the agarose has a melting point in the range of 55 to 65° C.

28. The cassette of claim 21, wherein the foam comprises a phenolic foam.

29. A cassette having a hollow for receiving and retaining a tissue specimen for fluid treatment preparatory to histological examination, comprising a top portion having a perforated bottom wall and a bottom portion snap or friction mounted to the top portion, the bottom portion having a side wall removable along a tear line, said cassette further comprising a pre-formed foam block and/or agarose in said hollow.

30. The cassette of claim 29, wherein said removable side wall bridges said top and bottom portions.

31. The cassette of claim 29, wherein said removable side wall includes a pair of tear lines.

32. The cassette of claim 29, wherein said removable side wall includes a projecting tab to facilitate removal of said side wall.

33. The cassette of claim 29, wherein said top and bottom portions are molded of a synthetic plastic material.

34. The cassette of claim 29, further comprising both agarose and a pre-formed foam block in said hollow.

35. The cassette of claim 29, further comprising filter paper positioned in said hollow to retard egress of molten paraffin.

36. A method for preparing a tissue sample for analysis, comprising the steps of:
   (a) orienting the tissue sample in the cassette of claim 29;
   (b) embedding an oriented tissue sample in a porous embedding media; and
   (c) directly processing the embedded tissue sample with tissue processing reagents while maintaining the original orientation of the sample without a post-processing paraffin-embedding step.

37. The method of claim 36, wherein the tissue sample is oriented in an opening or depression formed in said pre-formed foam.

38. The method of claim 36, including the step of forming said opening or depression by cutting, drilling, punching or molding.

39. The method of claim 37, wherein the tissue sample is embedded flush with or below an outer surface of the pre-formed foam.

40. The method of claim 37, wherein the pre-formed foam comprises a preformed block of phenolic foam.

41. The method of claim 36, wherein said agarose has a melting point in the range of about 55 to 65° C.

42. The method of claim 36, further including the step of sectioning the embedded tissue sample following processing.

43. The method of claim 36, wherein said tissue processing reagents are selected from the group consisting essentially of aqueous formalin, water, xylene, alcohol and paraffin.

44. A hollow cassette for receiving and retaining a tissue specimen for fluid treatment preparatory to histological examination, comprising a top portion having a perforated bottom wall and a bottom portion snap or friction mounted to the top portion, the bottom portion having a side wall removable along a tear line, the hollow being filled, at least in part, by a porous embedding medium, which comprises agarose and/or a pre-formed foam.

45. The cassette of claim 44, wherein said removable side wall bridges said top and bottom portions.

46. The cassette of claim 44, wherein said removable side wall includes a pair of tear lines.

47. The cassette of claim 44, wherein said removable side wall includes a projecting tab to facilitate removal of said side wall.

48. The cassette of claim 44, wherein said top and bottom portions are molded of a synthetic plastic material.

49. The cassette of claim 44, and further comprising filter paper positioned within the cassette to retard egress of molten paraffin.

50. The cassette of claim 44, wherein the agarose has a melting point in the range of 55 to 65° C.

51. The cassette of claim 44, wherein the foam comprises a phenolic foam.

* * * * *